United States Patent
Mowery et al.

(10) Patent No.: US 7,411,402 B2
(45) Date of Patent: Aug. 12, 2008

(54) TECHNIQUE FOR REDUCING A PARASITIC DC BIAS VOLTAGE ON A SENSOR

(75) Inventors: Kenneth D. Mowery, Noblesville, IN (US); Douglas J. Tackitt, Kokomo, IN (US)

(73) Assignee: Delphi Technologies, Inc., Troy, MI (US)

( * ) Notice: Subject to any disclaimer, the term of this patent is extended or adjusted under 35 U.S.C. 154(b) by 160 days.

(21) Appl. No.: 11/205,884

(22) Filed: Aug. 17, 2005

(65) Prior Publication Data
US 2007/0040103 A1   Feb. 22, 2007

(51) Int. Cl.
*G01N 27/26* (2006.01)
*G01R 27/26* (2006.01)

(52) U.S. Cl. .................. 324/464; 324/685
(58) Field of Classification Search .......... 324/464, 324/685
See application file for complete search history.

(56) References Cited

U.S. PATENT DOCUMENTS

| | | | |
|---|---|---|---|
| 4,571,543 A * | 2/1986 | Raymond et al. | 324/425 |
| 5,521,099 A * | 5/1996 | Glaunsinger et al. | 436/151 |
| 5,635,136 A * | 6/1997 | Glaunsinger et al. | 422/88 |
| 5,965,451 A * | 10/1999 | Plog et al. | 436/139 |
| 6,069,013 A * | 5/2000 | Plog et al. | 436/113 |
| 2005/0127920 A1* | 6/2005 | Mowery et al. | 324/464 |
| 2007/0056352 A1* | 3/2007 | Birkhofer et al. | 73/23.21 |

FOREIGN PATENT DOCUMENTS

WO    WO 2005003755 A1 *  1/2005

* cited by examiner

*Primary Examiner*—Timothy J Dole
(74) *Attorney, Agent, or Firm*—Jimmy L. Funke

(57) ABSTRACT

A technique for reducing a parasitic DC bias voltage on a sensor monitors the parasitic DC bias voltage on a first element of the sensor. A controlled bias voltage that is applied between the first element of the sensor and a second element of the sensor is then modified to substantially maintain the parasitic DC bias voltage at a desired potential.

11 Claims, 4 Drawing Sheets

TECHNIQUE FOR REDUCING A PARASITIC DC BIAS VOLTAGE ON A SENSOR

CROSS-REFERENCE TO RELATED APPLICATION

This application is related to U.S. patent application Ser. No. 10/966,109, entitled "METHOD AND SYSTEM FOR IMPEDANCE MEASUREMENT OF A ZEOLITE-BASED AMMONIA SENSOR," which was filed Oct. 15, 2004, which was published as US 2005/0127920 A1 on 16 Jun., 2005 and which is hereby incorporated herein by reference in its entirety.

TECHNICAL FIELD

The present invention is generally directed to a technique for reducing a DC bias on a sensor and, more specifically, to a technique for reducing a parasitic DC bias on a sensor.

BACKGROUND OF THE INVENTION

Various sensors have been developed to detect chemical elements and/or chemical compounds in a gas stream. For example, one Zeolite-based sensor exhibits a complex impedance that is dependent on the concentration of ammonia (NH3) in a gas stream presented to the sensor. In one particular implementation, a Zeolite-based sensor has been positioned within an exhaust gas stream of a diesel engine to provide feedback, as to the concentration of ammonia in the exhaust gas stream, to a control unit. Based upon the concentration of the ammonia in the exhaust gas stream, the control unit may cause reduction of the injection of urea, which acts to reduce nitrogen oxide (NOx) emission levels from the diesel engine, into the exhaust gas stream.

In many applications, in determining an impedance of a sensor it is undesirable to bias the sensor with a signal that has a direct current (IDC) component, as the DC component may cause ion migration or other chemical reactions in the sensor. Ion migration in a sensor may alter the impedance or other characteristics of the sensor, thereby providing an incorrect indication of the level of a gas within a gas stream. A traditional approach for determining the impedance of a sensor has utilized a system that has sourced a sinewave voltage excitation to an input of the sensor and has observed the resulting sinusoidal current. In general, such systems have captured both the amplitude and phase relationship of the sensor voltage and the sensor current, such that both a real and imaginary part of a sensor impedance could be determined.

In general, Zeolite-based sensing elements cannot be biased with any DC voltage component, as this causes ion migration in the Zeolite coated Inter-Digitated Capacitor (IDC) element of the sensor, which causes a parasitic shift of the impedance measurements. The impedance of the IDC element is typically measured with a 2000Hz sinewave signal. Typically, the circuits designed to measure the impedance of the gas-sensing cell in this sensor have been designed to minimize any DC leakage currents that would result in a charge on the Zeolite element.

Experimental data has shown that in spite of the efforts to minimize DC leakage currents, sizable amounts of nearly DC voltage can be built-up across the IDC element, due to inter-element leakage with the other sensor component cells. For example, a resistive temperature device (RTD) element that is placed in the sensor to provide feedback for the sensor temperature control function provides a well-known coupling mechanism. In general, the RTD element has been placed in the multi-layer sensor substrate structure, directly under the IDC element level, to achieve accurate temperature monitoring. The historical approach for controlling the effect of this parasitic coupling is to establish a known, fixed potential between the RTD and IDC elements. This potential has been empirically determined and locked into the interface electronics calibration. One issue with this technique is lack of repeatability of the "optimum" bias, due to dependence on sensor age, temperature and several lesser-known influences.

What is needed is a technique for reducing a parasitic DC bias voltage on a sensor, subject to ion migration, that acts to minimize the parasitic DC bias voltage on the sensor over the lifetime of the sensor.

SUMMARY OF THE INVENTION

Various embodiments of the present invention are directed to techniques for reducing a parasitic DC bias voltage on a sensor that may be subject to high-temperature induced ion migration within, for example, an alumina-based sensor structure. According to one embodiment, a voltage on a first element, e.g., an inter-digitated capacitor (IDC) element, of the sensor is filtered and a bias voltage between a second element, e.g., a resistive temperature device (RTD) element, of the sensor and the first element is periodically modified, based on the filtered voltage, to substantially maintain the bias voltage at zero potential. According to another embodiment, a parasitic DC bias voltage on a first element, e.g., an inter-digitated capacitor (IDC) element, of a sensor is filtered and a low-impedance path between a second element, e.g., a resistive temperature device (RTD) element, of the sensor and the first element is periodically provided, based on the filtered voltage, to substantially maintain the bias voltage at zero potential.

According to another aspect of the invention, the voltage on the IDC element is low-pass filtered. According to a different embodiment, the IDC element is coated with Zeolite. According to a different aspect, the low-pass filtered voltage is coupled to an input of a control unit and an output of the control unit provides a control signal that causes the bias voltage to be periodically modified. In various embodiments, the control unit may be configured as a proportional and integral controller.

These and other features, advantages and objects of the present invention will be further understood and appreciated by those skilled in the art by reference to the following specification, claims and appended drawings.

BRIEF DESCRIPTION OF THE DRAWINGS

The present invention will now be described, by way of example, with reference to the accompanying drawings, in which.

DESCRIPTION OF THE PREFERRED EMBODIMENTS

Various embodiments of the present invention are directed to techniques for reducing a parasitic DC bias voltage of a sensor. The parasitic DC bias voltage may be caused, for example, by ion migration within the sensor. According to one embodiment, a voltage on a first element, e.g., an inter-digitated capacitor (IDC) element, of the sensor is filtered and a bias voltage between a second element, e.g., a resistive temperature device (RTD) element, of the sensor and the first element is periodically modified, based on the filtered voltage, to substantially maintain the bias voltage at zero potential. According to another embodiment, a voltage on a first element, e.g., an inter-digitated capacitor (IDC) element, of a sensor is filtered and a low-impedance path between a second element, e.g., a resistive temperature device (RTD) element, of the sensor and the first element is periodically provided, based on the filtered voltage, to substantially maintain the bias voltage at zero potential.

According to another aspect of the present invention, the voltage on the IDC element is low-pass filtered. According to a different embodiment, the IDC element is coated with Zeolite. According to a different aspect, the low-pass filtered voltage is coupled to an input of a control unit and an output of the control unit provides a control signal that causes the bias voltage to be periodically modified. In various embodiments, the control unit may be configured as a proportional and integral (PI) controller.

Figure 1:
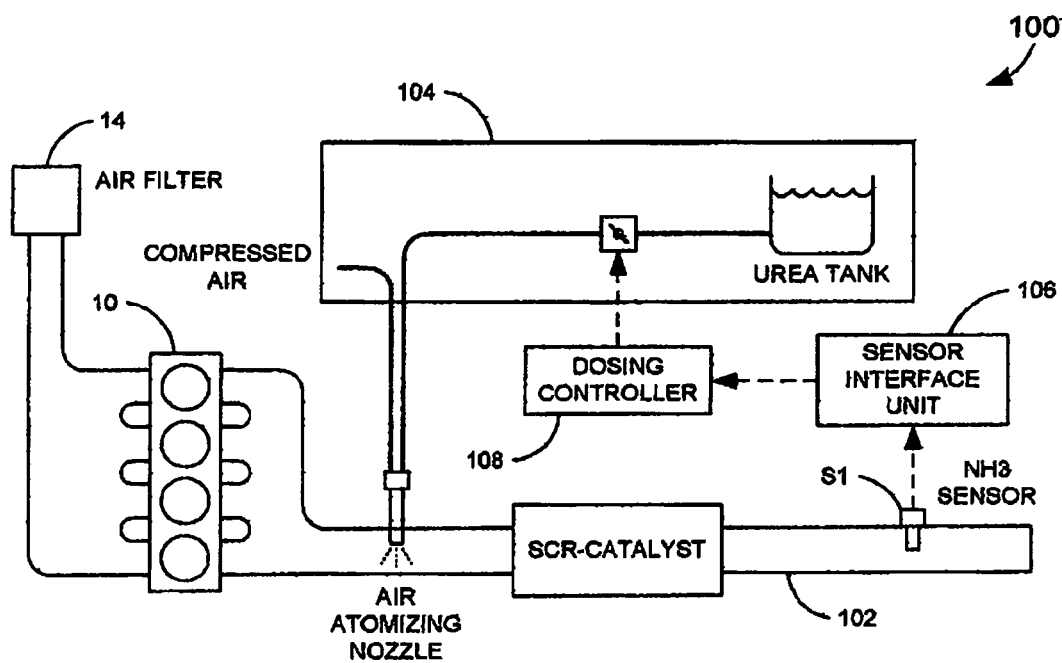
FIG. 1 is a diagram of an exemplary system for removing nitrogen oxide (NOx) from an exhaust stream of a diesel engine.

FIG. 1 depicts an exemplary system 100, which removes nitrogen oxide (NOx) from an exhaust gas associated with a diesel engine 10 of a motor vehicle. As is shown, a sensor S1, e.g., a Zeolite-based ammonia sensor, is positioned within an exhaust gas pipe 102 of the system 100 downstream of a selective catalytic reduction (SCR) catalyst. An ammonia sensor interface unit 106 is coupled to the sensor S1 and to a dosing controller 108. The ammonia sensor interface unit 106 provides an indication, which is based on the impedance of the sensor S1, to the dosing controller 108, as to the level of the ammonia in an exhaust gas stream associated with diesel engine 10.

When ammonia breakthrough is detected in the exhaust gas stream, the dosing controller 108 may command a treatment unit 104 to decrease the amount of a urea solution provided into the exhaust stream carried by the exhaust pipe 102. In this manner, the system 100 performs selective catalytic reduction (SCR) to remove nitrogen oxide (NOx) from the exhaust stream of the diesel engine 10, while monitoring for ammonia breakthrough.

Figure 2:
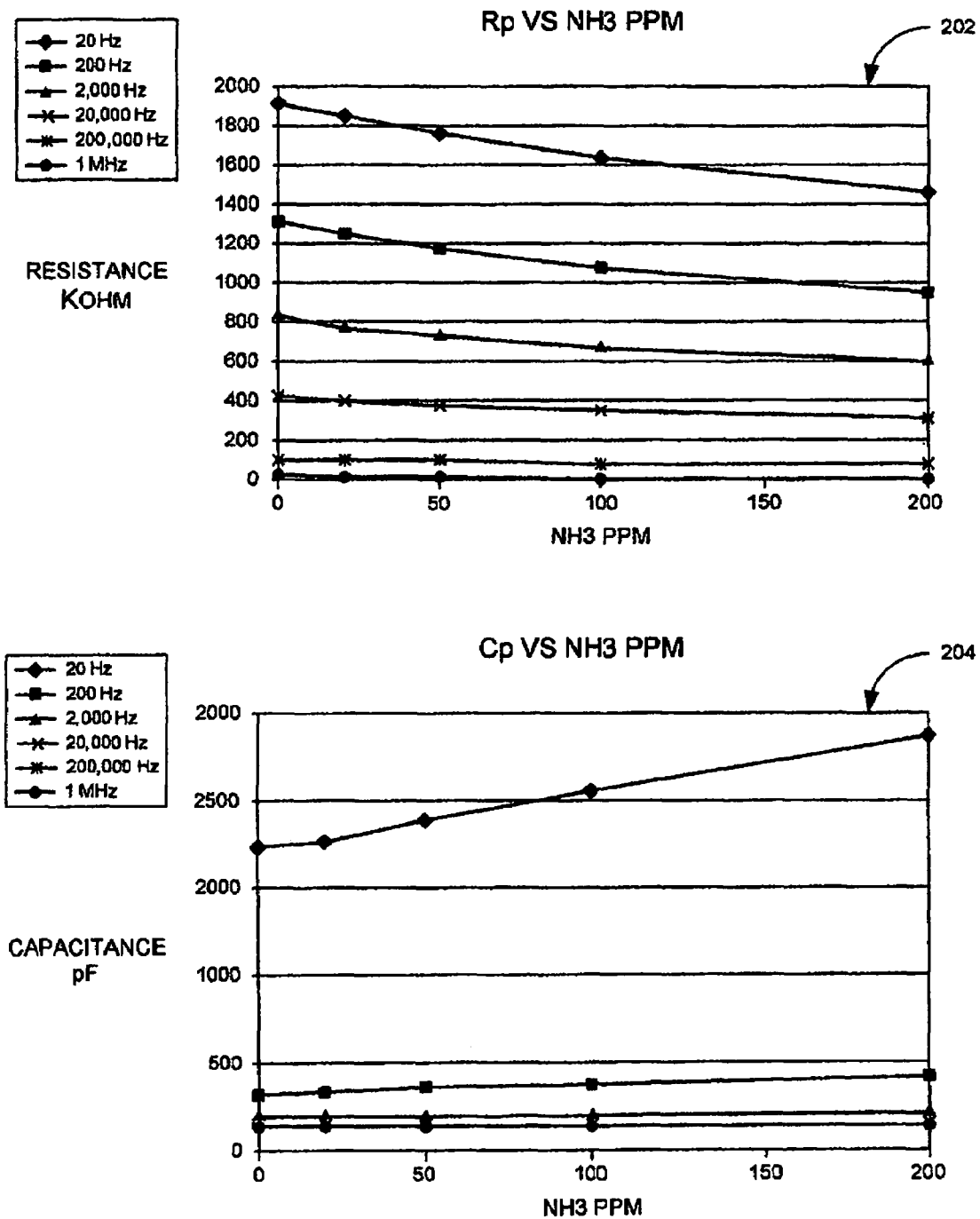
FIG. 2 is a chart depicting impedance curves for a sensor at different ammonia (NH3) concentrations.

With reference to FIG. 2, graphs 202 and 204 show a number of impedance curves of an exemplary Zeolite-based ammonia sensor. Each of the graphs 202 and 204 include impedance curves, which show that both of the real and imaginary parts of the impedance change with frequency and the concentration of NH3 in the gas sample being measured. This frequency dependence of both of these components points out the need to correctly select and control the actual times of the two waveform measurement samples to accurately calculate the real and imaginary parts of the sensor impedance and relate it to the desired indication of NH3 concentration.

Figure 3:
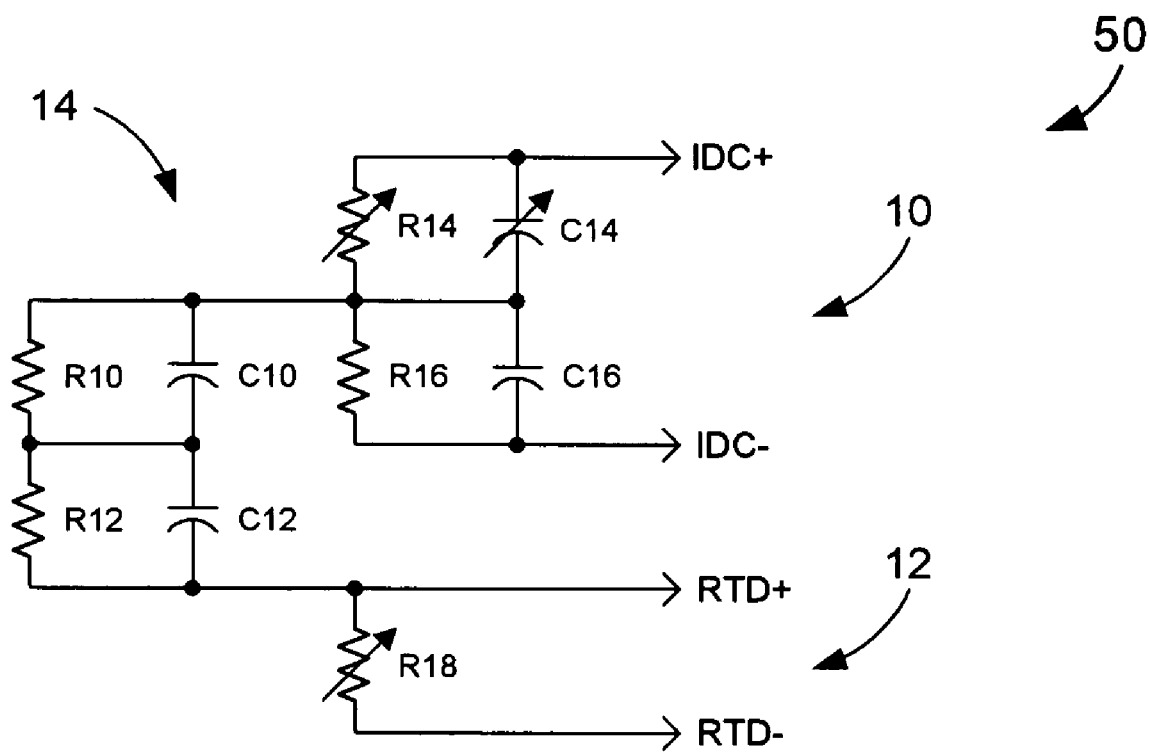
FIG. 3 is an exemplary electrical schematic that provides a behavioral model for an exemplary Zeolite NH3 sensor.

With reference to FIG. 3, a behavioral model 50 for an exemplary Zeolite NH3 sensor depicts a resistance temperature device (RTD) element to inter-digitated capacitor (IDC) element coupling mechanism within an exemplary physical structure for the sensor. The model 50 includes an IDC element 10, an RTD element 12 and a coupling mechanism element 14. As is shown, the IDC element 10 includes capacitors C14 and C16 and resistors R14 and R16. The RTD element 12 includes a variable resistor R18. The coupling mechanism 14 includes a network that includes resistors R10 and R12 and capacitors C10 and C12. As is depicted in FIG. 3, the resistor R14 and the capacitor C14 are variable. The exemplary values for the components of the behavioral model 50 indicate that the RTD element 12 to IDC element 10 coupling mechanism contains relatively long-time constants for the principal leakage path and that energy storage is present in the coupling mechanism 14. Additionally, any quasi-DC voltage that is developed across the IDC element 10 results in modification of the gain (i.e., sensitivity) of the main gas sensing parallel RC network, which includes the resistor R14 and the capacitor C14. The values listed for the various components of the model 50 represent typical mid-range values for an exemplary Zeolite-based sensor.

Figure 4:
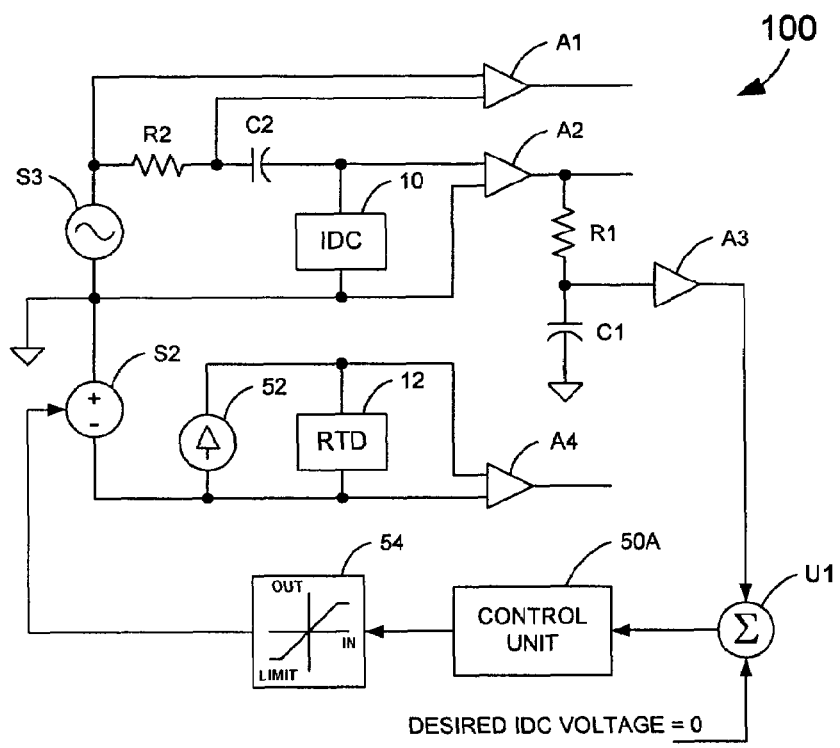
FIG. 4 is an exemplary electrical schematic depicting a control system for a sensor that maintains a quasi-DC voltage across an inter-digitated capacitor (IDC) element of the sensor near zero potential by modifying a bias voltage between the IDC element and a resistive temperature device (RTD) element.

As is shown in FIG. 4, a control system 101 includes a control unit 50A that is programmed to change a bias voltage provided by a voltage source S2 between the IDC element 10 and the RTD element 12. The system 101 maintains a quasi-DC voltage across the IDC element 10, at very nearly zero Volts, by actively modifying the bias voltage provided by the voltage source S2. As is shown, the control unit 50A utilizes a low-pass filtered version of the IDC output voltage to determine the bias voltage to apply between the elements 10 and 12. The control unit 50A may be, for example, a proportional and integral (PI) regulator that has its desired set point established at zero Volts and, in this manner, the control unit 50A acts to maintain short and long-term voltage across the IDC element 10 at approximately zero Volts.

It should be appreciated that this closed loop action nullifies any source of parasitic charge flow into the energy storage elements of the sensor structure and, in this manner, prevents polarization of the Zeolite material implemented in the sensor. It should also be appreciated that good engineering practices need to be applied to both the hardware and the software of the system 101 in order to manage the gain and phase relationships and to provide control stability.

As is depicted in FIG. 4, a comparator U1 receives an output from an amplifier A3, which is coupled across a capacitor C1, which is part of a low-pass filter that includes a resistor R1 and the capacitor C1, which is coupled to an AC voltage output of the sensor. Inputs of an amplifier A1 are coupled across a resistor R2. The output of the amplifier A1 provides a signal, which indicates the AC current of the sensor. An AC source S3 is coupled across the IDC element 10 by the resistor R2 and a capacitor C2. The output of the IDC element 10 is provided to an input of the an amplifier A2, whose output is coupled to one side of the resistor R1.

In parallel with the RTD element 12 is a constant current source 52, which biases the RTD element 12. An output of the RTD element 12 is fed to inputs of an amplifier A4, whose output provides an RTD signal. A desired IDC voltage signal, e.g., zero Volts, is applied to one input of a comparator U1. A second input of the comparator U1 is coupled to an output of the amplifier A3. The control unit 50A is designed to determine whether the IDC voltage is at a desired level and, if not, to take corrective action, by applying a bias control signal to a control input of the DC voltage source S2. If desired, a limiter 54 may be coupled between the control unit 50A and the control input of the source S2, so as to limit the voltage extremes of the voltage source S2.

According to the above-described approach, build-up of unwanted DC voltage on the IDC element 10 may be addressed, while still allowing a 2000Hz sinewave to be provided by the AC source S3, which is used for impedance measurement. As is discussed above, it should be appreciated that the control unit needs to utilize time sensitive software and hardware circuits to provide for proper control. In general, matching of time constants is not required and, as such, the time constants for the circuits and the algorithms may be selected for good system response and are not required to be tuned for each individual sensor. Thus, according to this embodiment of the present invention, the control system 101 includes impedance stability and repeatability with respect to NH3 gas concentration. Furthermore, measurement stability is improved by limiting charge polarization of the Zeolite material in the IDC element and automatic control may be implemented to allow for reduction or near elimination of a quasi-DC voltage on the IDC element.

Figure 5:
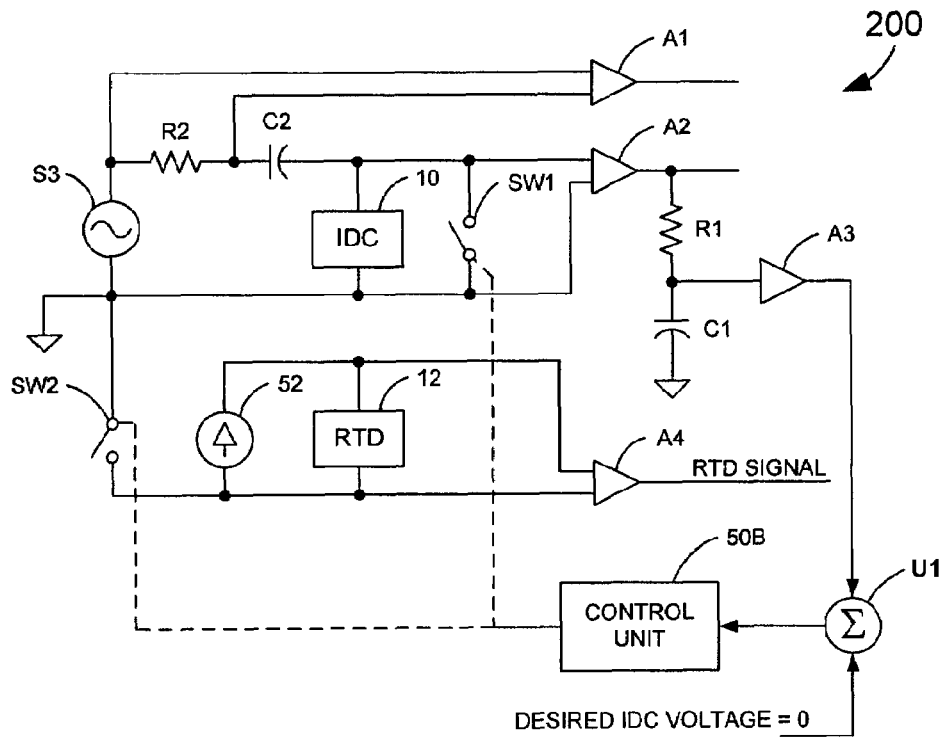
FIG. 5 is an exemplary electrical schematic depicting a sensor control system that maintains a quasi-DC voltage across an IDC element near zero potential by periodically providing a low-impedance path between the IDC element and a RTD element.

With reference to FIG. 5, a control system 200 that is similar to the control system 101 of FIG. 4 is depicted. However, instead of applying a bias voltage between the IDC element 10 and the RTD element 12, the control system 200 includes switches SW1 and SW2 that are controlled by control unit 50B to provide short circuits across the IDC element 10 and the RTD element 12 to the IDC element 10 coupling energy storage elements. It should be appreciated that the short circuits need to be removed, by the control unit 50B, prior to the re-establishment of the 2000Hz test sinewave voltage that is initiated to perform an impedance measurement. Furthermore, it should be appreciated that the interface electronics are required to settle out before a sensor reading is acquired. In a typical case, the sensor would be re-shorted periodically to maintain a discharged state on the RTD element to IDC element coupling components. The decision to apply the IDC discharge can be done either on a fixed time period basis or by using an on-demand approach by monitoring the output of the low-pass filter used to extract the average IDC voltage from the IDC signal.

Accordingly, a method and system have been described herein that advantageously provide a technique for maintaining an accuracy of a sensor, e.g., a Zeolite-based ammonia sensor, that may experience a parasitic DC bias voltage.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A method for reducing a parasitic DC bias voltage on a sensor, comprising the steps of:
   monitoring a parasitic DC bias voltage on a first element of a sensor; and
   modifying automatically a controlled bias voltage applied between the first element of the sensor and a second element of the sensor to substantially maintain the parasitic bias voltage of the first element at a desired potential,
   wherein the first element is an inter-digitated capacitor (IDC) element and the second element is a resistive temperature device (RTD) element and wherein the controlled bias voltage is modified to substantially maintain the parasitic DC bias voltage at zero potential in a closed loop,
   wherein the parasitic DC bias voltage on the IDC element is low-pass filtered,
   wherein the low-pass filtered parasitic DC bias voltage is coupled to an input of a control unit and an output of the control unit provides a control signal that causes the controlled bias voltage to be periodically modified, and
   wherein the control unit is configured as a proportional and integral controller.

2. The method of claim 1, wherein the IDC element is coated with Zeolite.

3. A method for reducing a parasitic DC bias voltage on a sensor, comprising the steps of:
   filtering a parasitic DC bias voltage on a first element of a sensor; and
   providing a low-impedance path between a second element of the sensor and the first element based on the filtered parasitic DC bias voltage to automatically substantially maintain the parasitic bias voltage at zero potential in a closed ioop, wherein the parasitic DC bias voltage is a feedback in the closed loopy,
   wherein the first element an inter-digitated capacitor (IDC) element and the second element is a resistive temperature device (RTD) element, and wherein the parasitic DC bias voltage on the IDC element is low-pass filtered,
   wherein the low-pass filtered parasitic DC bias voltage is coupled to an input of a control unit and an output of the control unit provides a control signal that causes the parasitic DC bias voltage to be periodically modified, and
   wherein the control unit is configured as a proportional and integral controller.

4. The method of claim 3, wherein the IDC element is coated with Zeolite.

5. A control system for reducing a parasitic DC bias voltage on a sensor subject to ion migration, comprising:
   a filter for filtering a parasitic DC bias voltage present on an inter-digitated capacitor (IDC) element of a sensor;
   a bias voltage source coupled between the IDC element and a resistive temperature device (RTD) of the sensor; and
   a control unit coupled to an output of the filter and an input of the bias voltage source, wherein the control unit provides a control signal on the input of the bias voltage source to modify a bias voltage provided by the bias voltage source between the RTD element and the IDC element based on the filtered voltage to automatically substantially maintain the parasitic DC bias voltage at zero potential in a closed loop, wherein the parasitic DC bias voltage is a feedback in the closed loop, and
   wherein the control unit is configured as a proportional and integral controller.

6. The system of claim 5, wherein the filter is a low-pass filter.

7. The system of claim 5, wherein the IDC element is coated with Zeolite.

8. A method for reducing a parasitic DC bias voltage on a sensor, comprising the steps of:
   monitoring a parasitic DC bias voltage on an inter-digitated capacitor (IDC) element;
   filtering the parasitic DC bias voltage on the IDC element by a low-pass filter; and
   modifying periodically a controlled bias voltage applied between the IDC element and a resistive temperature device (RTD) element of the sensor to substantially maintain the parasitic DC bias voltage at zero potential by a control unit, such that the low-pass filter is coupled to the control unit, and the control unit is configured as a proportional and integral controller.

9. A control system for reducing a parasitic DC bias voltage on a sensor subject to ion migration, comprising:
   a filter for filtering a parasitic DC bias voltage present on an inter-digitated capacitor (IDC) element of a sensor;
   a bias voltage source coupled between the IDC element and a resistive temperature device (RTD) of the sensor; and
   a control unit configured as a proportional and integral controller coupled to an output of the filter and an input of the bias voltage source, wherein the control unit provides a control signal on the input of the bias voltage source to modify a bias voltage provided by the bias voltage source between the RTD element and the IDC element based upon the filtered voltage to substantially maintain the parasitic DC bias voltage at zero potential.

10. The system of claim 9, wherein the filter is a low-pass filter.

11. The system of claim 9, wherein the IDC element is coated with Zeolite.

* * * * *